United States Patent [19]

Song

[11] 4,361,806

[45] Nov. 30, 1982

[54] METHOD USING AQUEOUS EMULSION HAVING MAGNETIZABLE PARTICLES FOR DETECTING FLAWS IN MAGNETIZABLE WORKPIECES

[75] Inventor: Sei H. Song, Des Plaines, Ill.

[73] Assignee: Magnaflux Corporation, Chicago, Ill.

[21] Appl. No.: 166,610

[22] Filed: Jul. 7, 1980

[51] Int. Cl.$^3$ .................... G01N 27/84; G01R 33/12
[52] U.S. Cl. .................................................. 324/216
[58] Field of Search ............... 324/214–216; 252/62.51, 62.52, 62.53

[56] References Cited

U.S. PATENT DOCUMENTS

| | | | |
|---|---|---|---|
| 2,267,999 | 12/1941 | Switzer | 175/183 |
| 2,936,287 | 5/1960 | Kazenas | 252/62.5 |
| 3,284,360 | 11/1966 | Peshin | 252/62.53 X |
| 3,404,093 | 10/1968 | Borrows | 252/62.52 |
| 3,445,759 | 5/1969 | Pevar | 324/216 |
| 3,485,758 | 12/1969 | Borucki et al. | 252/62.52 |
| 3,609,532 | 9/1971 | Van Kirk et al. | 324/38 |
| 3,786,346 | 1/1974 | Lorenzi | 324/216 |
| 3,978,398 | 8/1976 | Molina | 324/216 |
| 4,025,448 | 5/1977 | Sudol | 252/62.53 X |
| 4,145,300 | 3/1979 | Hendriks | 252/62.53 X |

FOREIGN PATENT DOCUMENTS

| | | | |
|---|---|---|---|
| 53-76090 | 7/1978 | Japan | 324/216 |
| 797335 | 7/1958 | United Kingdom | 324/216 |
| 316987 | 4/1970 | U.S.S.R. | 324/215 |

*Primary Examiner*—Gerard R. Strecker
*Attorney, Agent, or Firm*—Hill, Van Santen, Steadman, Chiara & Simpson

[57] ABSTRACT

Method and composition for non-destructive testing of a magnetizable workpiece wherein the surface of the workpiece is treated with an aqueous emulsion of a waxy solid having fluorescent magnetizable particles suspended therein, a magnetic field is created along the workpiece so that the magnetizable particles are attracted to imperfections therein, and then sufficient water is removed from the emulsion so that the waxy solid forms a film which contains the immobilized fluorescent particles which have become attached to imperfections in the workpiece. The film may be further protected by the application of finely divided abrasion resistant particles, such as glass beads or glass powder.

10 Claims, No Drawings

METHOD USING AQUEOUS EMULSION HAVING MAGNETIZABLE PARTICLES FOR DETECTING FLAWS IN MAGNETIZABLE WORKPIECES

BACKGROUND OF THE INVENTION

1. Field of the Invention

This invention is in the field of non-destructive testing of magnetizable workpieces wherein magnetic particles are used to detect the presence of seams and other imperfections. The specific improvement deals with the application of fluorescent magnetizable particles in the medium of a wax or resin type of aqueous emulsion thereby the film which deposits upon evaporation of the water holds the magnetizable particles in the flaw indication securely against the piece so that the workpiece can be handled roughly and still provide reasonably clear indications of imperfections.

2. Description of the Prior Art

Non-destructive testing procedures employing magnetic particles have been used for many years. More recently, the magnetic particles have been combined with fluorescent particles either in the form of a water or oil suspension, and the workpiece was inspected under filtered ultraviolet or black light to observe any concentration pattern of fluorescent particles caused by surface discontinuities. Prior art patents referring to this type of inspection technique include Switzer U.S. Pat. No. 2,267,999 and Kazenas U.S. Pat. No. 2,936,287. These patents relate, respectively, to lacquer bonded and resin bonded fluorescent magnetic particles for use in this type of inspection process.

Other prior art references which deal with the manufacture of the fluorescent coated magnetic particles, and the method of inspection using such particles are U.S. Pat. Nos. 3,404,093; 3,485,758; and 3,609,532, all assigned to the assignee of the present application.

The mganetic particle testing method is particularly applicable to the inspection of steel billets which are normally inspected in a continuous process in which the billet travels at relatively high velocity through a magnetizing yoke and through an applicator station where the fluorescent type magnetic particles are applied either in suspension or in dry form. It has been common practice to inspect such billets shortly after the magnetic particles were applied. Trained inspectors would thereupon mark any clusters of the magnetizable particles with a chalk or crayon, and leave the pieces for elimination of the defects either by scarfing or grinding.

Between the formation of the indication and the actual removal of the defective portion of the billet, the billet can be stored for an indefinite period of time, either indoors or outdoors. It may be moved more than once, and usually subject to very rough handling by bouncing along a roller conveyor, being pushed into a storage rack, or being picked up with electromagnets and then dropped into another location. Any indication that is not firmly fixed to the workpiece will no longer be visible after such rough handling.

SUMMARY OF THE INVENTION

The present invention provides an improved means for retaining fluorescent magnetic particle indications on the surface of a workpiece. By using a daylight fluorescent composition of sufficient visibility, the need for inspectors may actually be eliminated and flaws indicated by the brightly fluorscent deposits may be located readily by the shop personnel who have the responsibility of grinding or scarfing the surface to remove the flaws.

Specifically, the method of the present invention involves applying an aqueous emulsion of a film-forming waxy or resinous solid which has fluorescent magnetic particles suspended therein. In accordance with usual partice, the magnetizable workpiece is subjected to an electric current of sufficient intensity to create magnetic fields. The magnetizable particles are attracted to imperfections and, upon removal of some or most of the water from the emulsion, the film which deposits immobilizes the fluorescent particles which have become attached to such imperfections. In order to reduce the possibility of scraping the formed indications during transport, a coating of transparent, abrasion resistant particles such as glass beads or glass powder can be deposited on the coated test parts.

DESCRIPTION OF THE PREFERRED EMBODIMENTS

To achieve the best results of the present invention, it is advisable to employ a fluorescent magnetizable particle which can be readily observed under ordinary lighting conditions. For the purposes of this invention, I prefer to use a newly developed type of fluorescent magnetic particle which is described and claimed in copending Borrows application U.S. Ser. No. 94,764, filed Nov. 16, 1979, now U.S. Pat. No. 4,341,997. This application describes a composition for magnetic particle inspection which includes ferromagnetic core particles of a size ranging from about 25 to 150 microns (500 to 100 U.S. Standard Mesh) in maximum dimension, and daylight fluorescent pigment particles attached to the core. These particles can be attached to the core by encapsulation with a film-forming resin such as a polyamide resin which preferably contains a cascading opacifier. The fluorescent dye particles have a maximum dimension of at least 2 microns and may range from about 2 to 10 microns in maximum dimension. The maximum dimension of the ferromagnetic core particles is at least as great as the maximum dimension of the fluorescent pigment particles, and is preferably at least twice as great.

The cascading opacifier most frequently used is fluoranthene. This material has the property of absorbing rays in the ultraviolet region with the emission of additional visible light over and above what would be reflected if the substance were submitted to visible light radiation only.

The magnetic and fluorescent pigment particles and opacifier can be mixed in liquid suspension in a blender or colloid mill under sufficiently high shear to effect a cohesion between the various particles due to the operation of Van der Wall forces. In general, the blade of the blender of the rotor of the colloid mill are driven so as to rotate at a speed of at least 5400 and up to 7500 or even 12,000 rpm. Under the resulting shear due to high collision forces, the fluorescent pigment particles are cuased to adhere directly to the larger magnetic particles.

Encapsulation can be carried out through the use of a relatively long chain linear polyamide derived from the reaction of dimerized linoleic acid with diamines or other polyamines. Such polyamide resins are dissolved in isopropanol or other water miscible volatile organic solvents. The premixed magnetic powder, fluorescent pigments, and opacifier are then added slowly to the resulting solution to form a slurry.

The aqueous type emulsion which is used to suspend the fluorescent magnetizable particle can be any of a wide variety of aqueous emulsions which are available on the market. For example, one suitable material is "Wax Plate 139" marketed by S. C. Johnson & Son, Inc. This material is a water based wax emulsion having a solids content of about 24%, a pH of about 9.40, and a softening point of about 155° F. (68.3°C.). It has a viscosity of 15 to 20 cps. It can be applied by flow coating, immersion, wiping, or spraying.

Another suitable material is "Bright Plate 23" also put ut by S. C. Johnson & Son, Inc. This material is an acrylic polymer solution having a solids content of about 16%, and a pH of about 8.4.

"Wax-Plate 16" is another one of the Johnson wax products which can be employed for the purposes of the present invention. This material is a clear synthetic wax emulsion in water having a pH of about 9.6, a solids cntent of about 12%, and a viscosity at 100° F. (37.8°C.) of 1.9 centistokes.

Still another suitable waxy product is "Wax-Plate 14" which is a clear carnauba wax emulsion in water. It has a solids content of 20%, a pH of 8.5, and a melting point of 178° F. (81.1°C.).

"Wax-Plate 15", another product suitable for use in the present invention, is a clear polyethylene wax emulsion having a solids content of 25%, a pH of 10.0 and a melting point in excess of 220° F. (104.4° C.).

Another suitable film-forming resinous type material is "Rhoplex AC-33" marketed by Rohm and Hass Company. This material is an aqueous emulsion of an acrylic polymer having a solids content of 46% to 47%, a pH of about 9.4 to 9.9 and a density of 8.9 pounds per gallon. It can be applied by flow cating, immersion, wiping, or spraying.

The fluorescent magnetizable particles can be dispersed into the aqueous emulsion in amounts ranging from as little as 0.01 gram per liter to 100 grams per liter or more. The concentration of suspended solids in the composition will vary depending upon the avreage particle size of the fluorescent magnetic particles. For examle, powders can be used at a concentration of about 0.4 gram per liter for particles of 5 micron average diameter, or 0.8 grams per liter for particles averaging 30 to 40 microns in diameter.

Generally speaking, the film-forming solids should constitute from 10 to 50% by weight of the aqueous emulsion. The amount of solids can be further diluted if necessary, particularly if a very light spraying consistency is desired.

In operation, the dry workpiece to be inspected is passed through a standard magnetizing yoke of the type used in magnetic particle inspection processes. Then, the composition containing the fluorescent magnetizable particles suspended in the aqueous emulsion is applied by means of immersion, flow coating, spraying, or other means of application. The presence of the magnetic field in the imperfections causes the ferromagnetic particles to be attracted into clusters in such areas. Then, the water from the emulsion can be removed to a substantial extent as, for example, by using a blast of hot air. The evaporation of water is facilitated if the workpiece is preheated to an elevated temperature before application of the emulsion. The removal of the water causes the film-forming material to form a film which immobilizes the ferromagnetic particles making up the indication. In most cases, the fluorescence of the particles is sufficient to enable the defects to be seen with the naked eye, thus eliminating the need for an immediate inspection of the piece. Such indications will be retained on the surface of the piece despite normal rough handling and will be visible to shop personnel when it comes time to have such defects removed by grinding or scarfing. The coating can be easily removed from the surface of the piece by means of a hot alkaline solution or the like when desired.

The following specific compositions can be employed to achieve the benefits noted previously:

EXAMPLE 1

| | |
|---|---|
| Fluorescent magnetic particles | 1.498 g. |
| "Bright Plate 23" (solids content 16%) | 500 cc |
| Tap water   q.s. | 1000 cc |

EXAMPLE 2

| | |
|---|---|
| Fluorescent magnetic particles | 1.498 g. |
| "Wax Plate 16" (solids content 12%) | 500 cc |
| Tap water   q.s. | 1000 cc |

EXAMPLE 3

| | |
|---|---|
| Fluorescent magnetic particles | 1.498 g. |
| "Rhoplex AC-33" (solids content 46%) | 500 cc |
| Tap water   q.s. | 1000 cc |

EXAMPLE 4

| | |
|---|---|
| Fluorescent magnetic particles | 1.498 g. |
| "Rhoplex AC-33" | 250 cc |
| "Wax Plate 16" | 250 cc |
| Tap water   q.s. | 1000 cc |

In order to protect the indications further, it is advisable to apply a coating of transparent, abrasion resistant particles over the indications. Glass beads or glass powders ranging in size from 100 mesh (149 microns) to 200 mesh (74 microns) are particularly suitable for this purpose. Since the particles are transparent, they do not affect the brilliance of the fluorescent indications. While adhering to the waxy coating, the glass particles are hard enough to protect the indications from contact scraping. The particles also reduce tackiness where the waxy coating is applied to a hot surface. Such particles can be easily applied by means of an air spray.

It should be evident that various modifications can be made to the described embodiments without departing from the scope of the present invention.

I claim as my invention:

1. A method of non-destructive testing for a magnetizable workpiece which comprises:
   applying to the surface of said workpiece an aqueous emulsion of a waxy or resinous solid, said emulsion having fluorescent magnetizable particles suspended therein,
   creating a magnetic field along said workpiece so that the particles are attracted to imperfections therein,
   removing sufficient water from said emulsion so that said solid forms an adherent film containing immobilized fluorescent particles which have become attached to imperfections in said workpiece, and
   inspecting said workpiece for concentration patterns of magnetic particles located at said imperfections while said fluorescent particles remain adhered to said workpiece.

2. A method according to claim 1 in which said solid is a synthetic wax.

3. A method according to claim 1 in which said solid is a natural wax.

4. A method according to claim 1 in which said solid is polyethylene.

5. A method according to claim 1 in which said solid is an acrylic polymer.

6. A method according to claim 1 in which:
said fluorescent magnetizable particles include a ferromagnetic particle core, fluorescent pigment particles attached to said core, and a cascading opacifier.

7. A method according to claim 6 in which:
said core particles have a maximum dimension of from 25 to 150 microns.

8. A method according to claim 1 in which said solid constitutes from 10 to 50% by weight of said aqueous emulsion.

9. A method according to claim 1 in which includes the step of:
applying finely divided transparent, abrasion resistant particles over said film.

10. A method according to claim 9 in which:
said particles are glass beads or a glass powder.

* * * * *